United States Patent
Crotty et al.

(10) Patent No.: US 6,306,412 B1
(45) Date of Patent: *Oct. 23, 2001

(54) COSMETIC STRIP WITH AN AGENT FOR INDUCING A TEMPERATURE CHANGE

(75) Inventors: Brian Andrew Crotty, Branford; Craig Stephen Slavtcheff, Guilford; Alexander Paul Znaiden, Trumbull, all of CT (US)

(73) Assignee: Unilever Home & Personal Care USA, Division of Conopco, Inc., Greenwich, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/563,251

(22) Filed: May 1, 2000

Related U.S. Application Data

(60) Provisional application No. 60/148,772, filed on Aug. 13, 1999.

(51) Int. Cl.[7] ................................................. A01N 25/34
(52) U.S. Cl. .................... 424/402; 424/10.1; 424/400; 424/402; 424/443; 424/447; 424/448; 424/77
(58) Field of Search .................... 424/10.31, 401, 424/443, 446, 448, 77, 78.07; 514/952

(56) References Cited

U.S. PATENT DOCUMENTS

| 3,250,680 | 5/1966 | Menkart et al. . |
| 4,362,715 | 12/1982 | Strianse et al. . |
| 4,379,143 | 4/1983 | Sherry et al. . |
| 4,626,550 | 12/1986 | Hertzenberg . |
| 5,861,440 | 1/1999 | Gohla et al. . |

FOREIGN PATENT DOCUMENTS

| 2 205 303 | 11/1972 | (FR) . |
| 2 231 400 | 5/1973 | (FR) . |
| 11029434 | 2/1999 | (JP) . |
| 11299817 | 11/1999 | (JP) . |
| 11299818 | 11/1999 | (JP) . |
| 2000159633 | 6/2000 | (JP) . |
| 98/42303 | 10/1988 | (WO) . |
| 97/48387 | 12/1997 | (WO) . |

Primary Examiner—Thurman K. Page
Assistant Examiner—Charesse L. Evans
(74) Attorney, Agent, or Firm—Milton L. Honig

(57) ABSTRACT

An adhesive cosmetic strip is provided which includes a flexible water-insoluble substrate, an adhesive composition deposited onto the substrate and an agent interactive with water present in a sufficient quantity to induce a change of temperature of the strip. When applied to the skin, the strip is warmed by a reaction between water and an exothermic or endothermic agent held within the strip. Moisture within the skin or externally applied water penetrates the strip and will react with the agent to cause an increase or decrease in temperature.

13 Claims, No Drawings

COSMETIC STRIP WITH AN AGENT FOR INDUCING A TEMPERATURE CHANGE

This application claims benefit of provisional No. 60/148,772 filed Aug. 13, 1999.

BACKGROUND OF THE INVENTION

1. Field of the Invention

The invention concerns cosmetic dermal strips or patches which provide consumers with a temperature change as a sensorial signal.

2. The Related Art

Cosmetics are often provided with consumer perceivable sensorial signals. Most common of these signals are fragrances. Pleasing odor is often the single most important attribute inducing re-purchase by a consumer. Other sensorial attributes are also significant in cosmetic chemistry. Skinfeel of a product is highly important. Creams, lotions, gels and pastes often are judged for their efficacy by the tacticity of their feel. Silky, non-residue leaving cosmetics are much preferred over tacky ones, and the consumer may relate those aesthetics to actual pharmacological performance.

Sometimes the sensorial attribute is that of temperature. Coolness is imparted to toothpastes and aftershave lotions through the presence of camphor, menthol or menthol derivatives such as menthol lactate. Some formulations signal efficacy through a temperature increase. Inclusion of capsaicin, an alkaloid extracted from capsicum, gives a brief temperature rise sensation to the human neural system. Temperature sensations of the known art are relatively short lived. Mechanisms are necessary to extend the sensation.

Dermal patches or strips have recently become popular as delivery vehicle systems for cosmetic compositions. For instance, WO 98/42303 (Crotty et al.) describes a dry-to-the-touch keratotic plug remover strip. Upon wetting, the strip turns tacky and mobile. This product is placed on the bridge of the nose or other areas of the face requiring keratotic plug removal. Within a short time period, water evaporates from the wetted adhesive forming a dry film. The consumer must then peel the film from the face along with unwanted plugs bonded thereto. Amounts of water applied by the consumer may vary. Drying times are therefore also variable. A sensorial signal would be helpful for the consumer to know when to begin the peel removal.

Exothermic and endothermic reactions are other sources of temperature signaling. U.S. Pat. No. 5,861,440 (Gohla et al.) reports use of sugars, especially xylitol, for inducing a cooling sensation when contacted with water. Generation of exothermic heat is reported in U.S. Pat. No. 4,379,143 (Sherry et al.), U.S. Pat. No. 4,626,550 (Hertzenberg), U.S. Pat. No. 4,362,715 (Strianse et al.) and U.S. Pat. No. 3,250,680 (Menkart et al.). Each of these patents employ an aluminosilicate interacting with water to release momentary heat.

It is an object of the present invention is to provide cosmetic products, especially dermal strips or patches with an improved temperature sensorial signal.

Another object of the present invention is to provide cosmetic products, especially dermal strips or patches imparting a temperature change as a sensorial signal which may augment other sensory or emotive aesthetics of such products.

These and other objects of the present invention will become more readily apparent from consideration of the following summary and detailed discussion.

SUMMARY OF THE INVENTION

An adhesive cosmetic strip is provided for placement on skin which includes:

(i) a flexible water-insoluble substrate;

(ii) an adhesive composition deposited onto the substrate; and (iii) an agent interactive with water present in a sufficient quantity to induce a change of temperature in the strip of at least about 2° C.

DETAILED DESCRIPTION OF THE INVENTION

Now a temperature change sensorial signal has been found for use with dermal strips or patches. The invention is based upon the use of agents interactive with water that can be held for long periods of time close to the skin by incorporation into the adhesive portion of a strip or between layers of the strip. Water can be introduced to the area of treatment just prior to applying the patch. Alternatively the inherent moisture and sweat found on surfaces of the skin can serve to activate the agent thereby inducing a heat or cooling effect.

Flexible water-insoluble substrates are an essential element of the present invention. By "water insoluble" is meant that the substrate does not dissolve in or readily break apart upon immersion in water. A wide variety of materials can be used as the substrate.

Nonlimiting examples of suitable substrates include non-woven substrates, woven substrates, hydroentangled substrates, air entangled substrates and the like. Preferred embodiments employ nonwoven substrates since they are economical and readily available in a variety of materials. By nonwoven is meant that the layer is comprised of fibers which are not woven into a fabric but rather are formed into a sheet, particularly a tissue. The fibers can either be random (i.e., randomly aligned) or they can be carded (i.e. combed to be oriented in primarily one direction). Furthermore, the nonwoven substrate can be composed of a combination of layers of random and carded fibers.

Nonwoven substrates may be comprised of a variety of materials both natural and synthetic. By natural is meant that the materials are derived from plants, animals, insects or byproducts. By synthetic is meant that the materials are obtained primarily from various man-made materials or from material that is usually a fibrous web comprising any of the common synthetic or natural textile-length fibers, or mixtures thereof.

Nonlimiting examples of natural materials useful in the present invention are silk fibers, keratin fibers and cellulosic fibers. Nonlimiting examples of keratin fibers include those selected from the group consisting of wool fibers, camel hair fibers, and the like. Nonlimiting examples of cellulosic fibers include those selected from the group consisting of wood pulp fibers, cotton fibers, hemp fibers, jute fibers, flax fibers, and mixtures thereof. Wood pulp fibers are preferred.

Nonlimiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers and mixtures thereof. Examples of some of these synthetic materials include acrylics such as Acrilan®, Creslan®, and the acrylonitrile-based fiber, Orlon®; cellulose ester fibers such as cellulose acetate, Arnel®, and Acele®; polyamides such as Nylons (e.g., Nylon 6, Nylon 66, Nylon 610 and the like); polyesters such as Fortrel®, Kodel®, and the polyethylene terephthalate fibers, Dacron®; polyolefins such as polypropylene, polyethylene; polyvinyl acetate fibers and mixtures thereof.

Nonwoven substrates made from natural materials consist of webs or sheets most commonly formed on a fine wire screen from a liquid suspension of the fibers.

Nonwoven substrates made from synthetic materials useful in the present invention can be obtained from a wide variety of commercial sources. Nonlimiting examples of suitable nonwoven layer materials useful herein include HEF 40-047, an apertured hydroentangled material containing about 50% rayon and 50% polyester, and having a basis weight of about 43 grams per square yard (gsy), available from Veratec, Inc., Walpole, Mass.; HEF 140-102, an apertured hydroentangled material containing about 50% rayon and 50% polyester, and having a basis weight of about 56 gsy, available from Veratec, Inc., Walpole, Mass.; Novenet® 149–191, a thermo-bonded grid patterned material containing about 69% rayon, about 25% polypropylene, and about 6% cotton, and having a basis weight of about 100 gsy, available from Veratec, Inc., Walpole, Mass.; HEF Nubtex® 149–801, a nubbed, apertured hydroentangled material, containing about 100% polyester, and having a basis weight of about 70 gsy, available from Veratec, Inc. Walpole, Mass.; Keybak® 951V, a dry formed apertured material, containing about 75% rayon, about 25% acrylic fibers, and having a basis weight of about 43 gsy, available from Chicopee Corporation, New Brunswick, N.J.; Keybak® 1368, an apertured material, containing about 75% rayon, about 5% polyester, and having a basis weight of about 39 gsy, available from Chicopee Corporation, New Brunswick, N.J.; Duralace® 1236, an apertured, hydroentangled material, containing about 100% rayon, and having a basis weight from about 40 gsy to about 115 gsy, available from Chicopee Corporation, New Brunswick, N.J.; Duralace® 5904, an apertured, hydroentangled material, containing about 100% polyester, and having a basis weight from about 40 gsy to about 115 gsy, available from Chicopee Corporation, New Brunswick, N.J.; Sontaro® 8868, a hydroentangled material, containing about 50% cellulose and about 50% polyester, and having a basis weight of about 60 gsy, available from Dupont Chemical Corp.

Substrates of the present invention need not be formed of fibers. They may be cast as plastic films such as polyethylene, polyester, polyurethane, polyvinyl chloride, polyamide, cellophane, or metallic foils.

The water insoluble substrates of the present invention can comprise two or more layers. They may be of similar construction or have different texture and abrasiveness. The differing textures can result from the use of different combinations of materials or from the use of a substrate having a smooth surface and a more abrasive opposite surface. Combinations of hydrophilic and hydrophobic layers may be useful for certain products of this invention. Likewise there may be desired combination of fluid absorptive and non-absorptive layers.

A further important element of cosmetic strips according to the present invention is that of an adhesive composition deposited onto the substrate. The adhesive may be of the pressure sensitive variety or may be a dry-to-the-touch film whose tacticity is generated by adding a small amount of water at the point of use.

Pressure sensitive adhesives may be formed from a variety of natural and synthetic adhesive polymers. The natural ones may be based on starch or modified starches. Synthetic adhesives include polyvinyl acetate, polyvinyl chloride, polyurethane, polyamide, but most especially acrylic-based polymers. The acrylics may be homo- or co-polymers (the latter indicating at least two different monomer units within the polymer chain). Typical monomers for use in acrylic-based polymers include acrylic acid, methacrylic acid, ethylacrylate, methylacrylate, butylacrylate and combinations thereof. These may be obtained under the trademark Gelva® series sold by Monsanto and the Duro-Tak® series sold by the National Starch and Chemical Company. Most preferred are acrylic polymers available from Lohmann Therapie Systeme, Germany. Silicone-based polymers may also be employed such as Bio-Psa silicones sold by the Dow Corning Corporation.

Release or backing liners are usually placed over the adhesive layer. The release liner should have a surface that is easily stripped off or released prior to use of the strip. Suitable materials for this liner include polyvinylchloride, polyester, polyvinylidene chloride, polystyrene, polyethylene and paper, all of which are preferably but not necessarily coated with a silicone formulation.

Another type of adhesive suitable for the present invention is a dry-to-the-touch substance. Products based on this technology are often intended as keratotic plug (e.g. blackhead) removers from facial pores. In a dry state, the adhesive composition is non-tacky to the touch. The adhesive is activated by either directly wetting the composition on the sheet or indirectly by wetting the face in areas to be contacted by the composition. In either instance, the wetting agent interacts with the adhesive composition so it becomes tacky and sufficiently mobile to flow into skin pores. Pure water is the preferred wetting agent. However, other fluid systems or gels could be employed. Suitable fluids would include alcohols such as ethanol, propanol, propylene glycol, polyethylene glycol, polypropylene glycol and especially mixtures of these alcohols with water. Gels would normally consist of fluid (particularly water) and structuring agents such as Carbomer.

Subsequent to wetting, the adhesive composition is allowed to dry over the area of treatment. During drying keratotic plugs stickingly adhere to the composition. Advantageously the drying period ranges from 1 minute to 5 hours, preferably from 5 minutes to 1 hour, optimally from 10 to 20 minutes. Thereafter, the dried composition with adhered plugs is peeled from the skin.

The dry-to-the-touch adhesive composition will include a polymer which may either be anionic, nonionic, cationic, amphoteric or mixtures thereof. Further, there may be utilized combinations of different polymers from within the same type. Examples of nonionic polymers suitable for film deposition are the copolymers of vinyl acetate and crotonic acid, terpolymers of vinyl acetate, crotonic acid and a vinyl ester of an alpha-branched saturated aliphatic monocarboxylic acid such as vinyl neodecanoate; copolymers of methyl vinyl ether and maleic anhydride (molar ratio about 1.1) wherein such copolymers are 50% esterified with a saturated alcohol containing from 1 to 4 carbon atoms such as ethanol or butanol; and acrylic copolymers, terpolymers, etc., containing acrylic acid or methacrylic acid, esters of acrylic or methacrylic acid with one or more saturated alcohols having from 1 to 22 carbon atoms such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate, glycols having from 1 to 6 carbon atoms such as hydroxypropyl methacrylate and hydroxyethyl acrylate, styrene, vinyl caprolactam, vinyl acetate, acrylamide, alkyl acrylamides and methacrylamides having 1 to 8 carbon atoms in the alkyl group such as methacrylamide, t-butyl acrylamide and n-octyl acrylamide, and other compatible unsaturated monomers. One specific example is the emulsion polymerized terpolymer of methacrylic acid, n-butyl acrylate and ethyl acrylate (e.g., in a weight percent ratio of 31:42:27, respectively).

Further examples of nonionic film forming adhesive polymers are homopolymers of N-vinylpyrrolidone and copolymers of N-vinylpyrrolidone with compatible nonionic monomers such as vinyl acetate and terpolymers of ethyl acrylate, butyl methacrylate and methyl methacrylate. Nonionic polymers containing N-vinylpyrrolidone in various weight average molecular weights are available commercially from ISP Corporation such as homopolymers of N-vinylpyrrolidone having an average molecular weight of about 630,000 under the trademark PVP K-90 and those having an average molecular weight of about 1,000,000 sold under the trademark of PVP K-120. Particularly preferred is poly(methyl vinyl ether/maleic anhydride) as an unneutralized resin available from ISP Corporation under the trademark Gantrez® S-97 BF and polyvinylformamide available from the National Starch and Chemical Company, Division of ICI.

Anionic film forming adhesive polymers often are derived from the nonionic types which include carboxylic acid functions. Alkaline agents are employed to neutralize the carboxylic acid or anhydride transforming them into anionic salts. Examples of suitable neutralizing agents include 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanolamine (DIPA); triisopropanolamine (TIPA); and dimethyl stearamine (DMS). Most preferred is AMP.

Particularly preferred anionic polymers are the salts of poly(methyl vinyl ether/maleic anhydride) and polystyrene sulfonic acid. The former is obtained by at least partial neutralization of Gantrez® S-97 BF and the latter available from the National Starch & Chemical Company under the trademarks Versa TL-501 and Flexan® 130 having respective molecular weights of about 500,000 and 100,000. Other polymer films which may be employed and are commercially available are listed in the Table below.

TABLE

| POLYMER TRADEMARKS (SUPPLIER) | CTFA DESIGNATIONS |
|---|---|
| Resyn ® 28–1310 (NSC) | Vinyl acetate/crotonic acid copolymer |
| Resyn ® 28–2930 (NSC) | Vinyl acetate/crotonic acid/vinyl neodecanoate copolymer |
| Resyn ® 28–2913 (NSC) | Vinyl acetate/crotonic acid/vinyl neodecanoate copolymer |
| Versatyl ® 40 (NSC) | Octylacrylamide/acrylates copolymer |
| Versatyl ® 42 (NSC) | Octylacrylamide/acrylates copolymer |
| Experimental Resin (NSC) | Vinyl acetate/vinyl neodecanoate/maleic half-ester |
| Ultrahold-8 ® (BASF) | Acrylate/acrylamide copolymer |
| Luviset ® CAP (BASF) | Vinyl acetate/crotonic acid/vinyl propionate copolymer |
| PVP K-30 (ISP) | PVP |
| PVP/VA E-335 (ISP) | PVP/Vinyl acetate copolymer |
| PVP/VA E-735 (ISP) | PVP/Vinyl acetate copolymer |
| Gantrez ® ES-225 (ISP) | Ethyl ester of PVM/MA copolymer |
| Gantrez ® ES-425 (ISP) | Butyl ester of PVM/MA copolymer |
| Gaffix ® VC-713 (ISP) | Vinyl caprolactam/PVP/dimethyl aminoethyl methacrylate copolymer |

TABLE-continued

| POLYMER TRADEMARKS (SUPPLIER) | CTFA DESIGNATIONS |
|---|---|
| | aminoethyl methacrylate copolymer |

Cationic adhesive polymers suitable for the present invention may be prepared as homo- or copolymers from monomers including:

Dimethyl aminoethyl acrylate (DMAEA), Dimethylaminoethyl methacrylate (DMAEMA), Dimethylaminopropylacrylamide (DMAPAAm), and Dimethylaminopropyl methacrylamide (DMAPMAAm) which are all (meth)acrylamides or (meth)acrylic acid esters having a dialkylamino group;

Dimethylaminostyrene (DMASt) and Dimethyaminomethylstyrene (DMAMSt) and the like which are styrenes having a dialkylamino group;

4-Vinyl pyridine and 2-vinyl pyridine which are vinyl pyridines; and

Quaternized products of these with a known quaternizing agent such as alkyl halide, benzyl halide, alkyl or aryl sulfonic acid, or dialkyl sulfate.

Among suitable amphoteric adhesive polymers are those derived from monomers such as:

N-(3-sulfopropyl)-N-acryloyloxyethyl-N,N-dimethylammonium betaine, N-(3-sulfopropyl)- N-methacroylamidepropyl-N,N-dimethylammonium betaine, N-(3-carboxymethyl)-N-methacroylamidepropyl-N,N-dimethylammonium betaine and N-carboxymethyl-N-methacroyloxyethyl-N,N-dimethylammonium betaine.

When the salt forming group of the cationic and amphoteric polymers is not ionized, it is preferred to ionize it via neutralization with known acids such as hydrochloric acid and sulfuric acid which are inorganic acids; acetic acid, propionic acid, lactic acid, succinic acid, glycol acid which are organic acids, or with known bases such as triethylamine, trimethylamine which are tertiary amines; ammonia; or sodium hydroxide.

Relative amounts of water-insoluble substrate to adhesive composition may vary in the relative weight range from about 1,000:1 to about 1:1,000, preferably from about 100:1 to about 1:100, optimally from 20:1 to about 1:20, more optimally from about 5:1 to about 1:5 by weight.

A further element of the present invention is in an agent interactive with water to generate a change of temperature, the agent being admixed with the adhesive polymer. These agents should be capable of an exothermic or endothermic temperature jump of at least about 2° C., preferably about 5° to about 30° C., more preferably from about 80° to about 20° C., even more preferably from about 10° to about 15° C.

Illustrative of the exothermic reaction inducing agents are anhydrous silica, activated alumina, aluminosilicates (e.g. zeolites) and combinations thereof. Particularly preferred are aluminosilicates such as Zeolite A available from PQ Corporation and Cab-O-Sil® fumed silica available from the Cabot Corporation. Examples of endothermic agents are ammonium chloride and xylitol. Amounts of these substances may range from about 1 to about 80%, preferably from about 10 to about 60%, optimally from about 15 to about 40% by weight of the adhesive composition. When incorporating a water sensitive temperature change inducing agent, precaution should be employed to maintain the strip within packaging (e.g. sealed pouch or packet) that avoids exposure to moisture or at least excessive moisture.

A variety of skin treatment agents may be formulated with the adhesive compositions. These agents may include moisturizers, preservatives, herbal extracts, vitamins, anti-irritant agents, emulsifiers and keratolytic agents.

Polyhydric alcohols also known as polyols are the most useful moisturizers. Representative polyols include glycerine, diglycerine, propylene glycol, dipropylene glycol, polypropylene glycol, polyethylene glycol and derivatives thereof, sorbitol, hydroxypropyl sorbitol, hexylene glycol, 1,2-butylene glycol, 1,2,6-hexanetriol, isoprene glycol, 2-methyl-1,3-propanediol, ethoxylated glycerol, propoxylated glycerol and mixtures thereof. Amounts of the polyol may range from about 0.1 to about 95%, preferably from about 1 to about 50%, more preferably from about 1.5 to about 20%, optimally from about 3 to about 10% by weight of the adhesive composition.

Preservatives can desirably be incorporated into the adhesive compositions to protect against the growth of potentially harmful microorganisms. Suitable preservatives include alkyl esters of para-hydroxybenzoic acid, hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. Preservatives are preferably employed in amounts ranging from about 0.01% to about 2% by weight of the composition.

Herbal extracts may include Roman Chamomile, Green Tea, Sculicap, Nettle Root, Swertia Japonica, Fennel, Anise, Arnica, Calandula, Coltsfoot, Cornflower, Elder, Gentian, Hawthorn, Lavender, Linden, Myrrh, Oat, Rose, Sweet Clover, Sandalwood, Vetiver, Tulsi, Kamala, Eucalyptus, St. John's Wort and Aloe Vera extracts. Amount of each of the extracts may range from about 0.00001 to about 1%, preferably from about 0.01 to about 0.5%, optimally from about 0.05 to about 0.2% by weight of the adhesive composition.

Vitamins useful in products of the present invention include Vitamin E Acetate, Vitamin C, Vitamin A Palmitate, Panthenol and any of the Vitamin B complexes. Anti-irritant agents may also be present including those of alpha-bisabolol and potassium glycyhrrizzinate, each vitamin or anti-irritant agent being present in amounts ranging from about 0.001 to about 0.5%, preferably from about 0.01 to about 0.1% by weight of the adhesive composition.

Emulsifiers may also be incorporated into the cosmetic strips of this invention. These emulsifiers may be anionic, nonionic, cationic, amphoteric and combinations thereof. Useful nonionic type emulsifiers include the $C_{10}$–$C_{20}$ fatty alcohol or acid hydrophobes condensed with from 2 to 100 moles of ethylene oxide or propylene oxide per mole of hydrophobe; $C_2$–$C_{10}$ alkyl substituted phenols condensed with from 2 to 20 moles of alkylene oxide; mono- and di-fatty acid esters of ethylene glycol; fatty acid monoglyceride; sorbitan, mono- and di-$C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic emulsifiers. Amounts of the emulsifiers may range from about 0.1 to about 30%, preferably from about 0.5 to about 10% by weight of the adhesive composition.

Keratolytic agents may also be incorporated into the adhesive compositions. Typical of these agents are the alpha and beta hydroxycarboxylic acids. The alpha-hydroxycarboxylic acids include glycolic acid, malic acid, lactic acid and mixtures thereof as well as their salts such as alkali metal and ammonium salts. The most preferred beta hydroxycarboxylic acid is salicylic acid. Amounts of these keratolytic agents may range from about 0.01 to about 15%, preferably from about 1 to about 12% by weight of the adhesive composition.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated.

EXAMPLE 1

A dry-to-the-touch strip is prepared for use in removing keratotic plugs from skin pores. The strip employed is a 70:30 rayon/polyester nonwoven fabric available from Dupont. Poly(methyl vinyl ether maleic anhydride), commercially available as Gantrez S-97® is employed as the adhesive. The resin is dispersed in water along with titanium dioxide, silica and 2-amino-2-methyl-1-propanol (AMP). The mixture is coated by a knife-over-roll onto the nonwoven substrate. After coating, the strip and adhesive composition are dried at 75° C. in a convection oven. The dried sheet is then cut into small strips. The adhesive composition is dry-to-the-touch and has a composition as listed in Table I.

TABLE I

| COMPONENT | WEIGHT % |
| --- | --- |
| Gantrez S-97 ® | 62.0 |
| Anhydrous Silica | 20.0 |
| AMP | 7.0 |
| Titanium Dioxide | 1.0 |

EXAMPLE 2

Another dry-to-the-touch strip for removing keratotic plugs from skin pores is prepared employing a polyester/cellulose wet layed nonwoven fabric. Poly(vinylformamide) available from the National Starch and Chemical Company is taken as the adhesive in combination with anhydrous silica, titanium dioxide, Vitamin C (ascorbic acid), glycerin, dimethicone copolyol, methoxypropyl glucamide and disodium EDTA. The mixture is coated by a knife-over-roll onto the nonwoven substrate. After coating, the strip and adhesive composition are dried at 75° C. in a convection oven. The dried sheet is then cut into small strips. The adhesive composition is dry-to-the-touch and has a composition as listed in Table II.

TABLE II

| COMPONENT | WEIGHT % |
| --- | --- |
| Polyvinylformamide | 52.0 |
| Anhydrous Silica | 42.0 |
| Glycerin | 1.5 |
| Dimethicone Copolyol | 1.3 |
| Vitamin C | 1.0 |
| Titanium Dioxide | 1.0 |
| Disodium EDTA | 0.8 |
| Methoxypropylglucamide | 0.4 |

Just prior to use, the dry adhesive side of the resultant cosmetic strip is wetted. Anhydrous silica present in the composition reacts with the water generating a substantial exotherm delivering a warming sensorial signal.

EXAMPLE 3

This example illustrates a cationic type dry-to-the-touch strip used for the removal of keratotic plugs from skin pores. The substrate employed is a 100% cellulose non-woven fabric. Components of the adhesive as listed under Table III are combined in isopropanol with stirring and after full dispersion of the components coated onto the cellulose substrate. Thereafter the system is dried to remove the isopropanol solvent. The dried sheet is then cut into small strips.

A consumer utilizes the strips by wetting face and then applying the strip to the face. Heat is generated by reaction of water with anhydrous zeolite. The temperature increase signals the time period necessary for maturation (drying) of strip over the skin pores. Once dried, the strip is peeled. Plugs adhere to the peel being thereby removed from the pores.

TABLE III

| COMPONENT | WEIGHT % |
| --- | --- |
| Poly-2-acrylamide-2-methylpropane sulphonate | 34.0 |
| Zeolite | 45.0 |
| Glycerin | 15.0 |
| Perfume | 5.0 |
| Polyoxyethylene Hydrogenated Castor Oil (60 EO Adduct) | 1.0 |

EXAMPLE 4

This example illustrates an embodiment utilizing a pressure sensitive adhesive type of dermal patch for Vitamin C (antioxidant/anti-aging) benefit delivery. A silicone pressure sensitive adhesive is prepared by condensing at about 115° C. a siloxane resin copolymer with hydroxyl terminated polydimethyl siloxane in xylene solution in the presence of anhydrous ammonium. The resultant silicone adhesive in an amount of 55% is combined with 40% finely powdered silica and 5% ascorbic acid. The combination is deposited onto a polypropylene film to form a dermal patch. A Mylar® backing sheet is placed over the pressure-sensitive adhesive composition for storage and shipping purposes.

Just prior to use, the Mylar® backing is removed. Water is applied to an area of the skin onto which the patch is to be placed. Heat generated by the reaction of water with the zeolite signals a user that the patch formula is actively at work on the skin.

EXAMPLE 5

Another pressure sensitive adhesive strip is prepared for topical treatment of acne. A breathable polyurethane film (Bertek Medfilm 390) serves as a substrate sheet for an adhesive composition. An easy release silicon coated polystyrene film is then placed over the adhesive layer. The final thickness of the dried matrix is between 75 and 150 $\mu$m. Circular patches are then cut from the resultant multi-layered laminate. The formulation of the adhesive composition is outlined under Table IV. Moisture in the skin penetrates the patch, reacts with the aluminosilicate and thereby generates an exotherm. The heat signals that the acne treatment is progressing actively.

TABLE IV

| COMPONENT | WEIGHT % |
| --- | --- |
| Polyacrylic Adhesive Resin | 67.4 |
| Sodium Aluminosilicate | 30.0 |
| Salicylic Acid | 0.6 |
| Glycolic Acid | 0.5 |
| Sorbitan Monooleate | 0.5 |
| Alpha-bisabolol | 0.5 |
| Potassium Glycyrrhizinate | 0.5 |

EXAMPLE 6

An anti-wrinkle patch is formed by spreading a pressure-sensitive acrylic-based resin onto a cellulose non-woven substrate sheet. The sheet is dried in a convection oven to remove water. Mixed within the acrylic-based resin is 40% of powdered, finely dispersed zeolite and 2% lactic acid. A release liner film is applied over the adhesive. When ready for use, the liner is removed, and the adhesive strip applied to the face. Over several hours, perspiration penetrates the adhesive layer, interacts with the zeolite and thereby emits a heat of reaction. The heat indicates to a user the minimum time required for the strip to release its active amount of lactic acid agent.

The foregoing description and examples illustrate selected embodiments of the present invention. In light thereof variations and modifications will be suggested to one skilled in the art, all of which are within the spirit and purview of this invention.

What is claimed is:

1. An adhesive cosmetic strip for placement on skin comprising:
   (i) a flexible water-insoluble substrate;
   (ii) an adhesive composition deposited onto the substrate; and
   (iii) an agent interactive with water present in the adhesive composition in an amount from at least about 40% by weight of the adhesive composition and in a sufficient quantity to induce a change of temperature in the strip of at least about 2° C., the adhesive composition allowing the substrate to adhere to skin.

2. The strip according to claim 1 wherein the adhesive is selected from a dry-to-the-touch or a pressure-sensitive tacky adhesive.

3. The strip according to claim 1 wherein the adhesive composition further comprises a skin treatment agent.

4. The strip according to claim 3 wherein the skin treatment agent is selected from the group consisting of herbal extracts, emulsifiers, Vitamins and keratolytic agents.

5. The strip according to claim 4 wherein the keratolytic agent is salicylic acid.

6. The strip according to claim 1 wherein the agent interactive with water is selected from the group consisting of anhydrous silica, activated alumina, alumino silicates and combinations thereof.

7. The strip according to claim 6 wherein the agent interactive with water is selected from ammonium chloride and xylitol.

8. A method for cooling skin comprising applying to the skin an adhesive cosmetic strip for placement on skin comprising:
  (i) a flexible water-insoluble substrate;
  (ii) an adhesive composition deposited onto the substrate; and
  (iii) an agent interactive with water present in the adhesive composition in an amount from about 1 to about 80% by weight of the adhesive composition and in a sufficient quantity to induce a reduction in temperature in the strip of at least about 2° C., the adhesive composition allowing the substrate to adhere to skin.

9. The method according to claim 8 wherein the agent interactive with water induces an endothermic reaction.

10. The method according to claim 8 wherein the adhesive is selected from a dry-to-the-touch or a pressure-sensitive tacky adhesive.

11. The method according to claim 8 wherein the adhesive composition further comprises a skin treatment agent.

12. The method according to claim 11 wherein the skin treatment agent is selected from the group consisting of herbal extracts, emulsifiers, vitamins and keratolytic agents.

13. The method according to claim 12 wherein the keratolytic agent is salicylic acid.

* * * * *